US009045800B2

(12) United States Patent
Semizarov et al.

(10) Patent No.: US 9,045,800 B2
(45) Date of Patent: Jun. 2, 2015

(54) METHODS AND COMPOSITIONS FOR IDENTIFYING, CLASSIFYING AND MONITORING SUBJECT HAVING BCL-2 FAMILY INHIBITOR-RESISTANT TUMORS AND CANCERS

(75) Inventors: Dimitri Semizarov, Chicago, IL (US); Tamar Uziel, Deerfield, IL (US); David Ching Siang Huang, Fitzroy North (AU); Mark F. van Delft, Toronto (CA); Christin Tse, Libertyville, IL (US); Richard R. Lesniewski, Collegeville, PA (US)

(73) Assignee: AbbVie Inc., North Chicago, IL (US)

( * ) Notice: Subject to any disclaimer, the term of this patent is extended or adjusted under 35 U.S.C. 154(b) by 717 days.

(21) Appl. No.: 12/704,165

(22) Filed: Feb. 11, 2010

(65) Prior Publication Data

US 2010/0234239 A1 Sep. 16, 2010

Related U.S. Application Data

(60) Provisional application No. 61/151,749, filed on Feb. 11, 2009.

(51) Int. Cl.
*C12Q 1/68* (2006.01)
*C12P 21/06* (2006.01)

(52) U.S. Cl.
CPC ........ *C12Q 1/6886* (2013.01); *C12Q 2600/106* (2013.01); *C12Q 2600/156* (2013.01); *C12Q 2600/158* (2013.01)

(58) Field of Classification Search
USPC ................................. 435/6.1, 69.1
See application file for complete search history.

(56) References Cited

U.S. PATENT DOCUMENTS

| | | | |
|---|---|---|---|
| 4,582,788 | A | 4/1986 | Erlich |
| 4,683,194 | A | 7/1987 | Saiki et al. |
| 4,683,202 | A | 7/1987 | Mullis |
| 4,948,882 | A | 8/1990 | Ruth |
| 5,006,309 | A | 4/1991 | Khalil et al. |
| 5,063,081 | A | 11/1991 | Cozzette et al. |
| 5,089,424 | A | 2/1992 | Khalil et al. |
| 5,231,020 | A | 7/1993 | Jorgensen et al. |
| 5,424,414 | A | 6/1995 | Mattingly |
| 5,447,841 | A | 9/1995 | Gray et al. |
| 5,464,746 | A | 11/1995 | Fino |
| 5,491,224 | A | 2/1996 | Bittner et al. |
| 5,756,696 | A | 5/1998 | Gray et al. |
| 5,776,688 | A | 7/1998 | Bittner et al. |
| 6,395,472 | B1 | 5/2002 | Leary et al. |
| 2003/0170881 | A1 | 9/2003 | Davis et al. |
| 2003/0191300 | A1 | 10/2003 | Bennett et al. |
| 2004/0018577 | A1 | 1/2004 | Emerson Campbell et al. |
| 2005/0054078 | A1 | 3/2005 | Miller et al. |
| 2006/0160164 | A1 | 7/2006 | Miller et al. |
| 2008/0160545 | A1* | 7/2008 | McKeegan et al. .......... 435/7.23 |
| 2009/0143245 | A1* | 6/2009 | Gao et al. ..................... 506/12 |
| 2010/0144554 | A1 | 6/2010 | Semizarov et al. |

FOREIGN PATENT DOCUMENTS

| | | |
|---|---|---|
| EP | 50424 B1 | 9/1985 |
| EP | 84796 B1 | 5/1990 |
| EP | 237362 B1 | 3/1992 |
| EP | 201184 B1 | 12/1992 |
| EP | 258017 B1 | 6/1997 |
| WO | 2008/082673 | 7/2008 |
| WO | WO2008082643 A2 | 7/2008 |

OTHER PUBLICATIONS

Lock et al. Pediatric Blood Cancer (2008) 50: 1181-1189.*
Al-Harbi et al. Blood (2011) 118(13): 3579-3590.*
Kudoh et al. Clinical Cancer Research (1999) 5: 2526-2531.*
Kalioniemi, Anne. Current Opinion in Biotechnology (2008) 19: 36-40.*
Zhang et al. Cancer Research (2006) 66(9): 4627-4635.*
Placzek et al. Cell Death and Disease (2010) 1: e40.*
Kirkin et al. [Biochim. Biophys. Acta, vol. 1644, pp. 229-249 (2004)].*
Boise et al. [Cell, vol. 74, No. 4, pp. 597-608 (1993)].*
Ashman, et al., "Chromosomal Alterations in Small Cell Lung Cancer Revealed by Multicolour Fluorescence in Situ Hybridization", Int. J. Cancer, 102, 230-236, 2002.
Ausubel F. M., et al., "Current Protocols in Molecular Biology," Table of Contents, John Wiley & Sons, 2004.
Egholm, et al., "Peptide Nucleic Acids (PNA) Oligonucleotide Analogues with an Acbiral Peptide Backbone", American Chemical Society, 114, 1895-1897, 1992.
Chaudhary, et al., "Role of the Bcl-2 Gene Family in Prostate Cancer Progression and Its Implications for Therapeutic Intervention", Department of Histopathology, vol. 107, 49-57, 1999.
Cobleigh, et al., "Multinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," Journal of Clincal Oncology, vol. 17 No. 9, pp. 2639-2648, 1999.
Coe, et al., "Gain of a Region on 7p22.3, Containing MAD1L1, is the Most Frequent Event in Small-Cell Lung Cancer Cell Lines", Genes, Chromosomes & Cancer, vol. 45, 11-19, 2006.
Cory, S., et al., "The Bcl-2 family: roles in cell survival and oncogenesis", vol. 22, 8590-8607, 2003.
Fan, et al., "Molecular Cytogenetic", Table of Contents, Humana press, 2002.
Galteland, et al., "Translocation t(14;18) and gain of chromosome 18/Bcl2: effects on Bcl2 expression and apoptosis in B-cell non-Hodgkin's lymphomas", Leukemia, vol. 19, pp. 2313-2323, 2005.
International Search Report and Written Opinion for Application No. PCT/US2010/023818, Mailed on Jun. 16, 2010, 17 pages.
Jeffers, et al., "Puma is an essential mediator of p53-dependent and -independent apoptotic pathways", Cancer Cell, vol. 4, 321-328, 2003.

(Continued)

*Primary Examiner* — Ardin Marschel
(74) *Attorney, Agent, or Firm* — Lisa V. Mueller; Michael Best & Friedrich LLP

(57) ABSTRACT

The invention is directed to methods and kits that allow for identifying, classifying, and monitoring cancer patients for Bcl-2 family inhibitor therapies. The methods and compositions of the invention are directed to determining amplification of $Bcl-x_L$ and in cancer or tumor cells, or elevated $Bcl-x_L$ polypeptide expression.

22 Claims, No Drawings

(56) References Cited

OTHER PUBLICATIONS

Kim, et al., "Combined microarray analysis of small cell lung cancer reveals altered apoptotic balance and distinct expression signatures of MYC family gene amplification", Oncogene, vol. 25, 130-138, 2006.

Lynch, et al., "Activating Mutations in the Epidermal Growth Factor Receptor Underlying Responsiveness of Non-Small-Cell Lung Cancer to Gefitinib," N. Engl. J. Med, vol. 350, vol. 21, 2129-2139, 2004.

Martinez-Climent, et al., "Transformation of follicular lymphoma to diffuse large cell lymphoma is associated with a heterogeneous set of DNA copy number and gene expression alterations," Blood, vol. 101, 3109-3117, 2003.

Mullis K., et al., "Specific enzymatic amplification of DNA in vitro: the polymerase chain reaction," Cold Spring Harb. Symp. Quant. Biol., vol. 51 (Pt 1), pp. 263-273, 1986.

Monni, O., et al., "DNA copy number changes in diffuse large B-cell lymphoma-comparative genomic hybridization study," Blood, vol. 87, 5269-5278, 1996.

Nielson P. E., et al., "Sequence-selective recognition of DNA by strand displacement with a thymine-substituted polyamide," Science, vol. 254, pp. 1497-1500, 1991.

Nupponen, et al., "Genetic Alterations in Hormone-Refractory Recurrent Prostate Carcinomas", American Journal of Pathology, vol. 153 (1), 141-148, 1998.

Ohmori, et al., "Apoptosis of lung cancer cells caused by some anti-cancer agents (MMC, CPT-11, ADM) is inhibited by Bcl-2", Biophysical Research Communications, vol. 192(1), 30-36, 1993.

Olejniczak, et al., "Integrative Genomic Analysis of Small-Cell Lung Carcinoma Reveals Correlates of Sensitivity to Bcl-2 Antagonists and Uncovers Novel Chromosomal Gains", Mol. Cancer Res., vol. 5 (4), 331-339, 2007.

Oltersdorf, et al., "An inhibitor of Bcl-2 family proteins induces regression of solid tumours," Nature, 435 677-681, 2005.

Pauletti, et al., "Assessment of Methods for Tissue-Based Detection of the HER-2/neu Alteration in Human Breast Cancer: A Direct Comparison of Fluorescence in Situ Hybridization and Immunohistochemistry," Journal of Clinical Oncology, 18, pp. 3651-3664, 2000.

Shibue, et al., "Integral role of Noxa in p53-mediated apoptotic response", Genes & Dev., vol. 17, 2233-2238, 2003.

Tahir et al., "Influence of Bcl-2 Family Members on the Cellular Response of Small-Cell Lung Cancer Cell Lines to ABT-737," Cancer Research, pp. 1176-1183, vol. 67 (3), 2007.

Van Der Krol, A. R., et al., "Modulation of Eukaryotic Gene Expression by complementary RNA or DNA Sequences," BioTechniques, 6 (10), 958-976, 1988.

Van Delft, et al., "The BH3 mimetic ABT-737 targets selective Bcl-2 proteins and efficiently induces apoptosis via Bak/Bax if Mcl-1 is neutralized", Cancer Cell, vol. 10, 389-399, 2006.

Villunger, et al., "p53- and Drug-Induced Apoptotic Responses Mediated by BH3-Only Proteins Puma and Noxa", Science, vol. 302, pp. 1036-1038, 2003.

Yasui, et al., "Alteration in Copy Numbers of Genes as a Mechanism for Acquired Drug Resistance", Cancer Research, vol. 64, 1403-1410, 2004.

Zon G., "Oligonucleotide analogues as potential chemotherapeutic agents," Pharm. Res., 5 (9), 539-549, 1988.

* cited by examiner

SEQUENCE LISTING

```
<160> NUMBER OF SEQ ID NOS: 1

<210> SEQ ID NO 1
<211> LENGTH: 2575
<212> TYPE: DNA
<213> ORGANISM: Homo sapiens

<400> SEQUENCE: 1
ggaggaggaa gcaagcgagg gggctggttc ctgagcttcg caattcctgt gtcgccttct      60
gggctcccag cctgccgggt cgcatgatcc ctccggccgg agctggtttt tttgccagcc     120
accgcgaggc cggctgagtt accggcatcc ccgcagccac ctcctctccc gacctgtgat     180
acaaaagatc ttccggggc tgcacctgcc tgcctttgcc taaggcggat ttgaatctct      240
ttctctccct tcagaatctt atcttggctt tggatcttag aagagaatca ctaaccagag     300
acgagactca gtgagtgagc aggtgttttg gacaatggac tggttgagcc catccctatt     360
ataaaaatgt ctcagagcaa ccgggagctg gtggttgact ttctctccta caagctttcc     420
cagaaaggat acagctggag tcagtttagt gatgtggaag agaacaggac tgaggcccca     480
gaagggactg aatcggagat ggagacccc agtgccatca atggcaaccc atcctggcac     540
ctggcagaca gccccgcggt gaatggagcc actggccaca gcagcagttt ggatgcccgg     600
gaggtgatcc ccatggcagc agtaaagcaa gcgctgaggg aggcaggcga cgagtttgaa     660
ctgcggtacc ggcgggcatt cagtgacctg acatcccagc tccacatcac cccagggaca     720
gcatatcaga gctttgaaca ggtagtgaat gaactcttcc gggatggggt aaactggggt     780
cgcattgtgg ccttttttctc cttcggcggg gcactgtgcg tggaaagcgt agacaaggag     840
atgcaggtat tggtgagtcg gatcgcagct tggatggcca cttacctgaa tgaccaccta     900
gagccttgga tccaggagaa cggcggctgg gatacttttg tggaactcta tgggaacaat     960
gcagcagccg agagccgaaa gggccaggaa cgcttcaacc gctggttcct gacgggcatg    1020
actgtggccg gcgtggttct gctgggctca ctcttcagtc ggaaatgacc agacactgac    1080
catccactct accctcccac ccccttctct gctccaccac atcctccgtc cagccgccat    1140
tgccaccagg agaaccacta catgcagccc atgcccacct gccatcaca gggttgggcc    1200 cagatctggt cccttgcagc tagttttcta gaatttatca cacttctgtg agacccccac    1260
acctcagttc ccttggcctc agaattcaca aaatttccac aaaatctgtc caaaggaggc    1320
tggcaggtat ggaagggttt gtggctgggg gcaggagggc cctacctgat tggtgcaacc    1380
```

```
cttacccctt agcctccctg aaaatgtttt tctgccaggg agcttgaaag ttttcagaac    1440
ctcttcccca gaaaggagac tagattgcct ttgttttgat gtttgtggcc tcagaattga    1500
tcattttccc cccactctcc ccacactaac ctgggttccc tttccttcca tccctacccc    1560
ctaagagcca tttaggggcc acttttgact agggattcag gctgcttggg ataaagatgc    1620
aaggaccagg actccctcct cacctctgga ctggctagag tcctcactcc cagtccaaat    1680
gtcctccaga agcctctggc tagaggccag ccccacccag gagggagggg gctatagcta    1740
caggaagcac cccatgccaa agctagggtg gcccttgcag ttcagcacca ccctagtccc    1800
ttcccctccc tggctcccat gaccatactg agggaccaac tgggcccaag acagatgccc    1860
cagagctgtt tatggcctca gctgcctcac ttcctacaag agcagcctgt ggcatctttg    1920
ccttgggctg ctcctcatgg tgggttcagg ggactcagcc ctgaggtgaa agggagctat    1980
caggaacagc tatgggagcc ccagggtctt ccctacctca ggcaggaagg gcaggaagga    2040
gagcctgctg catggggtgg ggtagggctg actagaaggg ccagtcctgc ctggccaggc    2100
agatctgtgc cccatgcctg tccagcctgg gcagccaggc tgccaaggcc agagtggcct    2160
ggccaggagc tcttcaggcc tccctctctc ttctgctcca cccttggcct gtctcatccc    2220
caggggtccc agccaccccg ggctctctgc tgtacatatt tgagactagt ttttattcct    2280
tgtgaagatg atatactatt tttgttaagc gtgtctgtat ttatgtgtga ggagctgctg    2340
gcttgcagtg cgcgtgcacg tggagagctg gtgcccggag attggacggc ctgatgctcc    2400
ctcccctgcc ctggtccagg gaagctggcc gagggtcctg gctcctgagg ggcatctgcc    2460
cctcccccaa cccccacccc acacttgttc cagctctttg aaatagtctg tgtgaaggtg    2520
aaagtgcagt tcagtaataa actgtgttta ctcagtgaaa aaaaaaaaaa aaaaa         2575
```

METHODS AND COMPOSITIONS FOR IDENTIFYING, CLASSIFYING AND MONITORING SUBJECT HAVING BCL-2 FAMILY INHIBITOR-RESISTANT TUMORS AND CANCERS

CROSS-REFERENCE TO RELATED APPLICATIONS

This application claims the benefit of U.S. Ser. No. 61/151,749, filed on Feb. 11, 2009, the contents of which are herein incorporated by reference.

BACKGROUND OF THE INVENTION

1. Field of the Invention

This invention relates to diagnostic assays useful for identifying, classifying and monitoring cancer patients for Bcl-2 family inhibitor therapy, and in particular relates to measurement of certain markers that can identify patients whose cancer is likely to be resistant to most Bcl-2 inhibitors.

2. Description of Related Art

Genetic heterogeneity of cancer is a factor complicating the development of efficacious cancer drugs. Cancers that are considered to be a single disease entity according to classical histopathological classification often reveal multiple genomic subtypes when subjected to molecular profiling. In some cases, molecular classification proved to be more accurate than the classical pathology. The efficacy of targeted cancer drugs may correlate with the presence of a genomic feature, such as a gene amplification (Cobleigh et al., 1999; Lynch et al., 2004). For Her-2 in breast cancer, it has been demonstrated that detection of gene amplification provides superior prognostic and treatment selection information as compared with the detection by immunohistochemistry (IHC) of the protein over-expression (Pauletti et al., 2000). A need therefore exists for genomic classification markers that may improve the response rate of patients to targeted cancer therapy.

Lung cancer is an area of active research for new targeted cancer therapies. Lung malignancies are the leading cause of cancer mortality, approximately 160,000 deaths in the United States in 2006. Small-cell lung carcinoma (SCLC) is a histopathological subtype of lung cancer, which represents approximately 20% of lung cancer cases. The survival rate for this subtype is low (long-term survival 4-5%) and has not improved significantly in the past decade, despite the introduction of new chemotherapy regimens. The remainder of lung cancer cases are non-small-cell lung carcinomas (NSCLC), a category which is comprised of several common subtypes. In the past several years, there has been substantial progress in the development of targeted therapies for NSCLC, such as erlotinib and gefitinib. Genomic biomarkers have been discovered which enable stratification of NSCLC patients into potential responders and non-responders. In particular, mutations and amplifications in the EGFR kinase domain were shown to correlate with the response to erlotinib and gefitinib. Unfortunately, no such progress has been achieved with SCLC, even though genomic analysis of SCLC cell lines and tumors has been reported (Ashman et al., 2002; Coe et al., 2006; Kim et al., 2006).

Targeted cancer therapy research has been reported against members of the Bcl-2 protein family, which are central regulators of programmed cell death. The Bcl-2 family members that inhibit apoptosis are over-expressed in cancers and contribute to tumorigenesis. Bcl-2 expression has been strongly correlated with resistance to cancer therapy and decreased survival. For example, the emergence of androgen independence in prostate cancer is characterized by a high incidence of Bcl-2 expression (>40% of the cohort examined) (Chaudhary et al., 1999), which also corresponds to an increased resistance to therapy. Furthermore, over-expression of Bcl-2 in both NSCLC and SCLC cell lines, has been demonstrated to induce resistance to cytotoxic agents (Ohmori et al., 1993; Yasui et al., 2004). Yasui et al. (2004) describe copy number gain at the Bcl-w (BCL2L2) locus and conclude that Bcl-w expression is at least partially responsible for the chemoresistance of SKOV3/VP. Yatsui et al. (2004) does not disclose identification of Bcl-2 family copy number change in any other cancer cell line.

Martinez-Climent et al. (2003) describe identification of a copy number change at 18q21, including the Bcl-2 locus, in the transformation of follicular lymphoma to large cell lymphoma (Martinez-Climent et al., 2003). Monni et al. (1996) report multiple copy number changes in diffuse large B-cell lymphoma (Monni et al., 1996). Galteland et al. (2005) report gain of the chromosome locus of Bcl-2 in B-cell non-Hodgkin's lymphomas (Galteland et al., 2005). Nupponen, et al (1998) describe low level copy number gain of Bcl-2 in four of 17 samples of recurrent prostate cancer (Nupponen et al., 1998). Olejniczak et al. have reported a gain on 18q21 in SCLC that contained the Bcl-2 gene and was associated with sensitivity to a Bcl-2 inhibitor ABT-737 (Olejniczak et al., 2007).

A key area of oncology research today is the study of acquired resistance to targeted therapies. Targeted therapies provide undeniable benefits to patients; however, in most cases, these benefits are temporary, as tumors exact numerous strategies to escape the effects of these therapies. These resistance mechanisms are complex and diverse. Once understanding these mechanisms is achieved, new therapies that target resistance mechanisms can be developed and deployed.

BH3 mimetics are highly targeted compounds engineered to trigger apoptosis by inhibiting specific anti-apoptotic Bcl-2 family members. Resistance to the effects of these drugs may arise during treatment.

One such mimetic, ABT-737 (oral form, ABT-263), is a small-molecule inhibitor of the Bcl-2 family members Bcl-2, Bcl-$x_L$, and Bcl-w, and has been shown to induce regression of solid tumors (Oltersdorf et al., 2005). ABT-737 has been tested against a diverse panel of human cancer cell lines and has displayed selective potency against SCLC and lymphoma cell lines (Oltersdorf et al., 2005). ABT-737's chemical structure is provided by Oltersdorf et al. (2005) at p. 679.

In many tumors, the capacity of the Bcl-2 family to remove damaged cells is subverted, either because a pro-survival family member is over-expressed (Cory et al., 2003), or because mutations in the p53 pathway halt p53-mediated induction of the BH3-only proteins that would otherwise trigger apoptosis (Jeffers et al., 2003; Shibue et al., 2003; Villunger et al., 2003). Interestingly, however, even when resistant to Bcl-2 inhibitor family's effects, the apoptotic machinery in tumor cells remains intact.

In one study of cells that over-expressed pro-survival Bcl-2 family members, the cells were found to be resistant to ABT-737, which usually triggers Bax/Bak-mediated apoptosis. Van Delft et al. (2006) found that the cells were chemorefractive to ABT-737 because another pro-survival relative, Mcl-1, was over-expressed. By down-regulating Mcl-1, the cells became sensitive to ABT-737-mediated apoptosis (van Delft et al., 2006). The role of Mcl-1 in rendering a cancer cell refractory to ABT-737's effects was demonstrated by Tahir et al. (2007) (Olejniczak et al., 2007). In that study, Tahir et al. (2007) observed that as a small-cell lung cancer line was exposed to escalating doses of ABT-737, the cells acquired ABT-737 resistance, which was associated with up-regulation of Mcl-1 expression.

Thus there is a need to be able to identify cells that are resistant to antagonists of Bcl-2 family members.

BRIEF SUMMARY OF THE INVENTION

In a first aspect, the invention is directed to methods of classifying a patient having a cancer that is resistant to a Bcl-2 family inhibitor, comprising:
  (a) providing a tissue sample from a patient;
  (b) determining if a $Bcl-x_L$ gene is amplified; and
  (c) classifying the patient as resistant to the Bcl-2 small molecule inhibitor if the $Bcl-x_L$ gene is amplified.

In a second aspect, the invention is directed to methods for identifying a patient with cancer as eligible to receive a Bcl-2-family inhibitor therapy comprising:
  (a) providing a tissue sample from a patient;
  (b) determining if expression of a $Bcl-x_L$ gene is amplified; and
  (c) classifying the patient as eligible to receive the Bcl-2 family inhibitor if the $Bcl-x_L$ gene is not amplified.

In the first and second aspects, the Bcl-2 family inhibitor can be ABT-263, and amplification of the $Bcl-x_L$ gene correlates with an increase in expression of $Bcl-x_L$ polypeptide. The determining step can comprise in situ hybridization, such as with a nucleic acid probe that is detectably labeled. Alternatively, the PCR can be used to determine gene amplification, using primers that hybridize to the $Bcl-x_L$ gene. Amplification can also be determined using microarray assays.

In a third aspect, the invention is directed to methods of monitoring a patient being treated with an anti-Bcl-2-family agent comprising:
  (a) providing a test sample from a cancer patient;
  (b) identifying in or extracting from the test sample tumor or cancer cells;
  (c) determining in the tumor or cancer cells if a $Bcl-x_L$ gene is amplified; and
  (d) comparing number of tumor or cancer cells having an amplified $Bcl-x_L$ gene to baseline level of such tumor or cancer cells determined before or at onset of therapy.

In a fourth aspect, the invention is directed to methods of classifying a patient having a cancer that is resistant to a Bcl-2 family inhibitor, comprising:
  (a) providing a test sample from a patient;
  (b) determining in the test sample:
    (i) if $Bcl-x_L$ gene is amplified; and
    (ii) an amount of $Bcl-x_L$ in the test sample;
  (c) determining if the amount of $Bcl-x_L$ in the test sample is higher or lower then the amount of $Bcl-x_L$ in a control; and
  (d) classifying the patient as having a cancer that is resistant to the Bcl-2 family inhibitor based on:
    (i) amplification of the $Bcl-x_L$ gene; and
    (ii) the amount of $Bcl-x_L$ is higher in the test sample than in the control.

In a fifth aspect, the invention is directed to methods of identifying a patient with cancer as eligible to receive a Bcl-2-family inhibitor therapy comprising:
  (a) providing a test sample from a patient;
  (b) determining in the test sample:
    (i) if $Bcl-x_L$ gene is amplified; and
    (ii) an amount of $Bcl-x_L$ in the test sample;
  (c) determining if the amount of $Bcl-x_L$ in the test sample is higher or lower then the amount of $Bcl-x_L$ in a control; and
  (d) classifying the patient as eligible to receive the Bcl-2 family inhibitor therapy based on:
    (i) amplification of the $Bcl-x_L$ gene; and
    (ii) the amount of $Bcl-x_L$ is higher in the test sample than in the control.

In a sixth aspect, the invention is directed to methods of monitoring a patient being treated with an anti-Bcl-2-family agent comprising:
  (a) providing a test sample from a cancer patient;
  (b) identifying in or extracting from the sample tumor or cancer cells;
  (c) determining whether the patient should continue to be treated with the Bcl-2 family inhibitor based on the presence of absence of amplification of the $Bcl-x_L$ gene.

In a seventh aspect, the invention is directed to monitoring a patient being treated with an anti-Bcl-2-family agent comprising:
  (a) providing a test sample from a patient;
  (b) determining in the test sample:
    (i) if $Bcl-x_L$ gene is amplified; and
    (ii) an amount of $Bcl-x_L$ in the test sample;
  (c) determining if the amount of $Bcl-x_L$ in the test sample is higher or lower then the amount of $Bcl-x_L$ in a control; and
  (d) determining whether the patient should continue to be treated with the Bcl-2 family inhibitor based on:
    (i) if the $Bcl-x_L$ gene is amplified;
    (ii) if the amount of $Bcl-x_L$ is higher in the test sample than in the control.
  determining step (b)(ii) is performed by immunoassay.

In these first seven aspects of the invention, the Bcl-2 family inhibitor can be ABT-263, and amplification of the $Bcl-x_L$ gene correlates with an increase in expression of $Bcl-x_L$ protein, respectively. The determining step can comprise in situ hybridization, such as with a nucleic acid probe that is detectably labeled. Alternatively, the PCR can be used to determine gene amplification, using primers that hybridize to the $Bcl-x_L$ gene. Amplification can also be determined using microarray assays. In some aspects, $Bcl-x_L$ gene expression is determined by measuring mRNA or polypeptide levels. Polypeptide levels can be measured using immunoassays, such as sandwich immunoassays, ELISAs, or even using automated immunoassay instruments. The patients can suffer particularly from SLCL and lymphoma. The tumor cells can be circulating tumor cells.

In an eighth aspect, the invention is directed to kits comprising:
  (a) reagents to detect an amplified $Bcl-x_L$ gene; and
  (b) instructions.

The reagents in the kit can be detectably-labeled polynucleotides that hybridize to at least a portion of the $Bcl-x_L$ gene, or antibodies that bind $Bcl-x_L$ polypeptides.

BRIEF DESCRIPTION OF SEVERAL VIEWS OF THE DRAWINGS

Not applicable

DETAILED DESCRIPTION OF THE INVENTION

The present invention provides methods and compositions for monitoring cancer and tumor cells for resistance to Bcl-2 family inhibitor therapies. The inventors discovered, unexpectedly, that gene amplification of the region encoding one of the gene products already targeted by a Bcl-2 family inhibitor gave rise to Bcl-2 family inhibitor resistance. This finding was fully unanticipated in theory, or from the literature.

The inventors discovered the amplification by using a microarray-based comparative genomic hybridization technique to detect gene copy number abnormalities on a genomewide scale, thus providing a whole-genome view of chromosomal aberrations accompanied by a change in the DNA copy number. This method is fully disclosed in METHODS FOR ASSEMBLING PANELS OF CANCER CELL LINES FOR USE IN TESTING THE EFFICACY OF ONE OR MORE PHARMACEUTICAL COMPOSITIONS, filed Oct. 31, 2008 and assigned U.S. Ser. No. 61/110,281, which is incorporated herein by reference in its entirety.

The invention provides diagnostic assays for identifying, classifying and monitoring cancer patients which comprises assessing in a patient tissue sample Bcl-$x_L$ gene amplification and/or gene expression increase. The inventive assays include assay methods for identifying patients eligible to receive Bcl-2 family antagonist therapy and for monitoring patient response to such therapy. The invention comprises, for example, determining by fluorescent in situ hybridization the presence or absence of amplification of Bcl-$x_L$ gene. Patients classified as having an amplified Bcl-$x_L$ are ineligible to receive anti-Bcl-2 family therapy because they are less likely to respond to this therapy. In addition, patients having this amplification can be resistant to other cancer therapy. Thus, determination of the presence of an amplification of Bcl-$x_L$ in cancer and tumor cells is a general therapy stratification marker.

In one embodiment, the invention comprises a method for identifying or classifying a patient having a cancer that is resistant to a Bcl-2 family inhibitor, comprising:
(a) providing a tissue sample from a patient;
(b) determining if a Bcl-$x_L$ gene is amplified; and
(c) classifying the patient as resistant to the Bcl-2 small molecule inhibitor if the Bcl-$x_L$ gene is amplified.

In this embodiment, the gene amplification can determined by a multi-color fluorescent in situ hybridization (FISH) assay, for example, performed on a lung cancer tumor biopsy sample. In other embodiments, the polymerase chain reaction (PCR) is used.

In another embodiment, the invention is directed to methods for monitoring a patient being treated with an anti-Bcl-2-family agent comprising:
(a) providing a test sample from a cancer patient;
(b) identifying in or extracting from the test sample tumor or cancer cells;
(c) determining in the tumor or cancer cells if a Bcl-$x_L$ gene is amplified; and
(d) comparing number of tumor or cancer cells having an amplified Bcl-$x_L$ gene to baseline level of such tumor or cancer cells determined before or at onset of therapy.

Again, FISH and PCR methods can be used to detect Bcl-$x_L$ amplification.

The invention further comprises methods of classifying a patient having a cancer that is resistant to a Bcl-2 family inhibitor, comprising
(a) providing a test sample from a patient;
(b) determining in the test sample:
(i) if Bcl-$x_L$ gene is amplified; and
(ii) an amount of Bcl-$x_L$ in the test sample;
(c) determining if the amount of Bcl-$x_L$ in the test sample is higher or lower then the amount of Bcl-$x_L$ in a control; and
(d) classifying the patient as having a cancer that is resistant to the Bcl-2 family inhibitor based on:
(i) amplification of the Bcl-$x_L$ gene; and
(ii) the amount of Bcl-$x_L$ is higher in the test sample than in the control.

These same methods can be used to identify those patients who are eligible to receive a Bcl-2 family inhibitor therapy.

The invention is also directed to kits the package, for example, polynucleotides engineered to be used as PCR primers, FISH probes, etc.

The invention has significant capability to provide improved stratification of patients for cancer therapy, and in particular for Bcl-2 family inhibitor therapy. The assessment of these biomarkers with the invention also allows tracking of individual patient response to the therapy.

DEFINITIONS

A "Bcl-2 family inhibitor" refers to a therapeutic compound of any type, including small molecule-, antibody-, antisense-, small interfering RNA, or microRNA-based compounds, that binds to at least one of Bcl-2, Bcl-$x_L$, and Bcl-w, and antagonizes the activity of the Bcl-2 family related nucleic acid or protein. The inventive methods are useful with any known or hereafter developed Bcl-2 family inhibitor. An example of a Bcl-2 family inhibitor is ABT-737, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, which binds to each of Bcl-2, Bcl-$x_L$, and Bcl-w. Another Bcl-2 family inhibitor is ABT-263, N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide. The chemical structure of ABT-263 is related to ABT-737 and its chemical structure is shown in Formula (I):

(I)

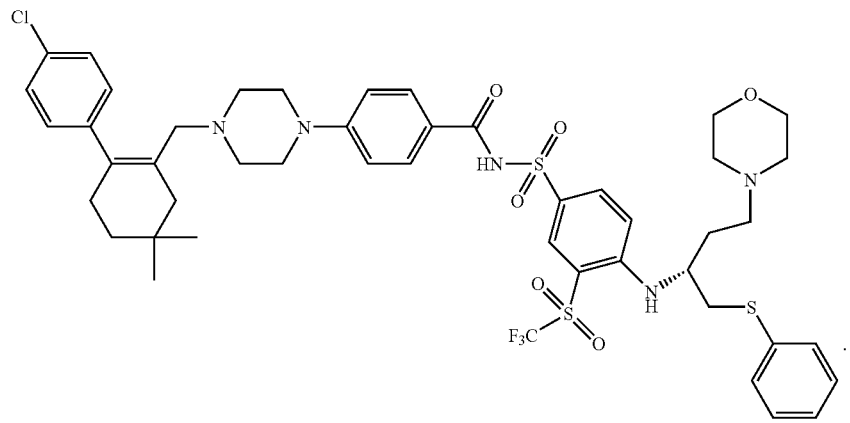

The assays of the invention can be used with targeted cancer therapy, such as targeted therapies to small cell lung cancer and lymphoma. The assays can be performed in relation to any cancer type in which amplification of Bcl-$x_L$ is involved. Other examples of such cancers include epithelial cancers, e.g., prostate cancer, ovarian and esophageal cancer. The inventive assays are performed on a patient tissue sample of any type or on a derivative thereof, including peripheral blood, tumor or suspected tumor tissues (including fresh frozen and fixed paraffin-embedded tissue), cell isolates such as circulating epithelial cells separated or identified in a blood sample, lymph node tissue, bone marrow and fine needle aspirates.

Bcl-2 (also known as BCL2) means the human B-cell CLL/lymphoma 2 gene; Bcl-xl (also known as BCL2L1) means the human BCL2-like 1 gene; Bcl-w (also known as BCL2L2) means the human BCL2-like 2 gene.

"Specifically hybridize" refers to the ability of a nucleic acid to bind detectably and specifically to a second nucleic acid. Polynucleotides specifically hybridize with target nucleic acid strands under hybridization and wash conditions that minimize appreciable amounts of detectable binding by non-specific nucleic acids.

"Target sequence" or "target nucleic acid sequence" means a nucleic acid sequence encompassing, for example, a gene, or complements or fragments thereof, that is amplified, detected, or both using a polynucleotide primer or probe. Additionally, while the term target sequence sometimes refers to a double stranded nucleic acid sequence; a target sequence can also be single-stranded. In cases where the target is double-stranded, polynucleotide primer sequences preferably amplify both strands of the target sequence. A target sequence can be selected that is more or less specific for a particular organism. For example, the target sequence can be specific to an entire genus, to more than one genus, to a species or subspecies, serogroup, auxotype, serotype, strain, isolate or other subset of organisms.

"Test sample" means a sample taken from a subject, or a biological fluid, wherein the sample may contain a target sequence. A test sample can be taken from any source, for example, tissue, blood, saliva, sputa, mucus, sweat, urine, urethral swabs, cervical swabs, urogenital or anal swabs, conjunctival swabs, ocular lens fluid, cerebral spinal fluid, etc. A test sample can be used (i) directly as obtained from the source; or (ii) following a pre-treatment to modify the character of the sample. Thus, a test sample can be pre-treated prior to use by, for example, preparing plasma or serum from blood, disrupting cells or viral particles, preparing liquids from solid materials, diluting viscous fluids, filtering liquids, adding reagents, purifying nucleic acids, etc.

"Subjects" include a mammal, a bird, or a reptile. The subject can be a cow, horse, dog, cat, or a primate. Subject can also be a human. Subjects can be alive or dead.

A "polynucleotide" is a nucleic acid polymer of ribonucleic acid (RNA), deoxyribonucleic acid (DNA), modified RNA or DNA, or RNA or DNA mimetics (such as PNAs), and derivatives thereof, and homologues thereof. Thus, polynucleotides include polymers composed of naturally occurring nucleobases, sugars and covalent inter-nucleoside (backbone) linkages as well as polymers having non-naturally-occurring portions that function similarly. Such modified or substituted nucleic acid polymers are well known in the art and are referred to as "analogues." Oligonucleotides are generally short polynucleotides from about 10 to up to about 160 or 200 nucleotides.

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with a given nucleic acid sequence. Variants do not encompass the native nucleotide sequence.

Ordinarily, variant polynucleotides are at least about 8 nucleotides in length, often at least about 9, 10, 11, 12, 13, 14, 15, 16, 17, 18, 19, 20, 21, 22, 23, 24, 25, 26, 27, 28, 29, 30, 35, 40, 45, 50, 55, 60 nucleotides in length, or even about 75-200 nucleotides in length, or more.

"Percent (%) nucleic acid sequence identity" with respect to nucleic acid sequences is defined as the percentage of nucleotides in a candidate sequence that are identical with the nucleotides in the sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

$$\% \text{ nucleic acid sequence identity} = W/Z*100$$

where

W is the number of nucleotides scored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

"Consisting essentially of a polynucleotide having a % sequence identity" means that the polynucleotide does not substantially differ in length, but may differ substantially in sequence. Thus, a polynucleotide "A" consisting essentially of a polynucleotide having at least 80% sequence identity to a known sequence "B" of 100 nucleotides means that polynucleotide "A" is about 100 nts long, but up to 20 nts can vary from the "B" sequence. The polynucleotide sequence in question can be longer or shorter due to modification of the termini, such as, for example, the addition of 1-15 nucleotides to produce specific types of probes, primers and other molecular tools, etc., such as the case of when substantially non-identical sequences are added to create intended secondary structures. Such non-identical nucleotides are not considered in the calculation of sequence identity when the sequence is modified by "consisting essentially of."

The specificity of single stranded DNA to hybridize complementary fragments is determined by the stringency of the reaction conditions. Hybridization stringency increases as the propensity to form DNA duplexes decreases. In nucleic acid hybridization reactions, the stringency can be chosen to favor specific hybridizations (high stringency). Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide, which decrease DNA duplex stability. A common approach is to vary the temperature: higher relative temperatures result in more stringent reaction conditions. (Ausubel et al., 1987) provide an excellent explanation of stringency of hybridization reactions.

Hybridization under "stringent conditions" means hybridization protocols in which nucleotide sequences at least 60% homologous to each other remain hybridized.

Polynucleotides can include other appended groups such as peptides (e.g., for targeting host cell receptors in vivo), or agents facilitating transport across the cell membrane. In addition, oligonucleotides can be modified with hybridization-triggered cleavage agents (van der Krol et al., 1988) or intercalating agents (Zon, 1988). The oligonucleotide can be conjugated to another molecule, e.g., a peptide, a hybridization triggered cross-linking agent, a transport agent, a hybridization-triggered cleavage agent, and the like.

Useful polynucleotide analogues include polymers having modified backbones or non-natural inter-nucleoside linkages. Modified backbones include those retaining a phosphorus atom in the backbone, such as phosphorothioates, chiral phosphorothioates, phosphorodithioates, phosphotriesters, aminoalkylphosphotriesters, methyl and other alkyl phosphonates, as well as those no longer having a phosphorus atom, such as backbones formed by short chain alkyl or cycloalkyl inter-nucleoside linkages, mixed heteroatom and alkyl or cycloalkyl inter-nucleoside linkages, or one or more short chain heteroatomic or heterocyclic inter-nucleoside linkages. Modified nucleic acid polymers (analogues) can contain one or more modified sugar moieties.

Analogs that are RNA or DNA mimetics, in which both the sugar and the inter-nucleoside linkage of the nucleotide units are replaced with novel groups, are also useful. In these mimetics, the base units are maintained for hybridization with the target sequence. An example of such a mimetic, which has been shown to have excellent hybridization properties, is a peptide nucleic acid (PNA) (Buchardt et al., 1992; Nielsen et al., 1991).

The realm of nucleotides includes derivatives wherein the nucleic acid molecule has been covalently modified by substitution, chemical, enzymatic, or other appropriate means with a moiety other than a naturally occurring nucleotide.

Polynucleotides comprise primers that specifically hybridize to target sequences, including analogues and/or derivatives of the nucleic acid sequences, and homologs thereof.

Polynucleotides can be prepared by conventional techniques, such as solid-phase synthesis using commercially available equipment, such as that available from Applied Biosystems USA Inc. (Foster City, Calif.; USA), DuPont, (Wilmington, Del.; USA), or Milligen (Bedford, Mass.; USA). Modified polynucleotides, such as phosphorothioates and alkylated derivatives, can also be readily prepared by similar methods known in the art (Fino, 1995; Mattingly, 1995; Ruth, 1990).

"Gene" refers to a nucleic acid fragment that expresses a specific protein, including regulatory sequences preceding (5' non-coding sequences) and following (3' non-coding sequences) the coding sequence.

"Native gene" refers to a gene as found in nature with its own regulatory sequences. In contrast, "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment).

A "probe" or "primer" as used herein is a polynucleotide that is at least 8 nucleotides in length and forms a hybrid structure with a target sequence, due to complementarity of at least one sequence in the probe or primer with a sequence in the target region. The polynucleotide regions of the probe can be composed of DNA and/or RNA and/or synthetic nucleotide analogs. Preferably, the probe does not contain a sequence that is complementary to the sequence or sequences used to prime for a target sequence during the polymerase chain reaction.

"Expression" refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

PCR is a powerful technique used to amplify DNA millions of fold, by repeated replication of a template, in a short period of time. ((Mullis et al., 1986); Erlich et al., European Patent Application No. 50,424; European Patent Application No. 84,796; European Patent Application No. 258,017, European Patent Application No. 237,362; European Patent Application No. 201,184, U.S. Pat. No. 4,683,202; U.S. Pat. No. 4,582,788; and U.S. Pat. No. 4,683,194). The process uses sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions can be analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

Practicing the Invention
Polynucleotide Assays

Nucleic acid assay methods useful in the invention comprise detection of amplified DNA regions by: (i) in situ hybridization assays to intact tissue or cellular samples, (ii) microarray hybridization assays to chromosomal DNA extracted from a tissue sample, and (iii) polymerase chain reaction (PCR) or other amplification assays to chromosomal DNA extracted from a tissue sample. Assays using synthetic analogs of nucleic acids, such as peptide nucleic acids, in any of these formats can also be used.

The assays of the invention are used to identify amplified Bcl-$x_L$ regions, resulting in an increase in Bcl-$x_L$ copy number biomarkers for both predicting therapy response and for monitoring patient response to Bcl-2 family inhibitor therapy. Assays for response prediction can be run before start of therapy, and patients showing an amplification in Bcl-$x_L$ region(s) are eligible to receive Bcl-2 family inhibitor therapy. The copy number gain can also indicate resistance to other cancer therapy, such as chemotherapy or radiation therapy. For monitoring patient response, the assay is run at the initiation of therapy to establish baseline levels of the biomarker in the tissue sample, for example, the percent of total cells or number of cells showing the copy number gain in the sample. The same tissue is then sampled and assayed and the levels of the biomarker compared to the baseline. Where the levels remain the same or decrease, the therapy is likely being effective and can be continued. Where significant increase over baseline level occurs, the patient may not be responding.

The invention comprises detection of the genomic biomarkers by hybridization assays using detectably labeled nucleic acid-based probes, such as deoxyribonucleic acid (DNA) probes or protein nucleic acid (PNA) probes, or unlabeled primers which are designed/selected to hybridize to the specific designed chromosomal target. The unlabeled primers are used in amplification assays, such as by polymerase chain reaction (PCR), in which after primer binding, a polymerase amplifies the target nucleic acid sequence for subsequent detection. The detection probes used in PCR or other amplification assays are preferably fluorescent, and still more preferably, detection probes useful in "real-time PCR". Fluorescent labels are also preferred for use in situ hybridization but other detectable labels commonly used in hybridization techniques, e.g., enzymatic, chromogenic and isotopic labels, can also be used. Useful probe labeling techniques are described in the literature (Fan, 2002) (incorporated by reference). In detection of the genomic biomarkers by microarray analysis, these probe labeling techniques are applied to label a chromosomal DNA extract from a patient sample, which is then hybridized to the microarray.

The polynucleotide sequence for human Bcl-$x_L$ (SEQ ID NO:1; GenBank Accession No. NM_138578) is shown in Table 1.

TABLE 1

Polynucleotide sequence of human Bcl-$x_L$
(SEQ ID NO: 1; Genbank Accession No. NM_138578)

| | | | | | |
|---|---|---|---|---|---|
| ggaggaggaa | gcaagcgagg | gggctggttc | ctgagcttcg | caattcctgt | gtcgccttct 60 |
| gggctcccag | cctgccgggt | cgcatgatcc | ctccggccgg | agctggtttt | tttgccagcc 120 |
| accgcgaggc | cggctgagtt | accggcatcc | ccgcagccac | ctcctctccc | gacctgtgat 180 |
| acaaaagatc | ttccgggggc | tgcacctgcc | tgcctttgcc | taaggcggat | ttgaatctct 240 |
| ttctctccct | tcagaatctt | atcttggctt | tggatcttag | aagagaatca | ctaaccagag 300 |
| acgagactca | gtgagtgagc | aggtgttttg | gacaatggac | tggttgagcc | catccctatt 360 |
| ataaaaatgt | ctcagagcaa | ccgggagctg | gtggttgact | ttctctccta | caagctttcc 420 |
| cagaaaggat | acagctggag | tcagtttagt | gatgtggaag | agaacaggac | tgaggcccca 480 |
| gaagggactg | aatcggagat | ggagaccccc | agtgccatca | atggcaaccc | atcctggcac 540 |
| ctggcagaca | gccccgcggt | gaatggagcc | actggccaca | gcagcagttt | ggatgcccgg 600 |
| gaggtgatcc | ccatggcagc | agtaaagcaa | gcgctgaggg | aggcaggcga | cgagtttgaa 660 |
| ctgcggtacc | ggcgggcatt | cagtgacctg | acatcccagc | tccacatcac | cccagggaca 720 |
| gcatatcaga | gctttgaaca | ggtagtgaat | gaactcttcc | gggatggggt | aaactggggt 780 |
| cgcattgtgg | cctttttctc | cttcggcggg | gcactgtgcg | tggaaagcgt | agacaaggag 840 |
| atgcaggtat | tggtgagtcg | gatcgcagct | tggatggcca | cttacctgaa | tgaccaccta 900 |
| gagccttgga | tccaggagaa | cggcggctgg | gatactttg | tggaactcta | tgggaacaat 960 |
| gcagcagccg | agagccgaaa | gggccaggaa | cgcttcaacc | gctggttcct | gacgggcatg 1020 |
| actgtggccg | gcgtggttct | gctgggctca | ctcttcagtc | ggaaatgacc | agacactgac 1080 |
| catccactct | accctcccac | cccttctct | gctccaccac | atcctccgtc | cagccgccat 1140 |
| tgccaccagg | agaaccacta | catgcagccc | atgccacct | gcccatcaca | gggttgggcc 1200 |
| cagatctggt | cccttgcagc | tagttttcta | gaatttatca | cacttctgtg | agacccccac 1260 |

TABLE 1-continued

Polynucleotide sequence of human Bcl-x$_L$
(SEQ ID NO: 1; Genbank Accession No. NM_138578)

```
acctcagttc ccttggcctc agaattcaca aaatttccac aaaatctgtc caaaggaggc  1320
tggcaggtat ggaagggttt gtggctgggg gcaggagggc cctacctgat tggtgcaacc  1380
cttacccctt agcctccctg aaaatgtttt tctgccaggg agcttgaaag ttttcagaac  1440
ctcttcccca gaaaggagac tagattgcct ttgttttgat gtttgtggcc tcagaattga  1500
tcattttccc cccactctcc ccacactaac ctgggttccc tttccttcca tccctacccc  1560
ctaagagcca tttaggggcc acttttgact agggattcag gctgcttggg ataaagatgc  1620
aaggaccagg actccctcct cacctctgga ctggctagag tcctcactcc cagtccaaat  1680
gtcctccaga agcctctggc tagaggccag ccccacccag gagggagggg gctatagcta  1740
caggaagcac cccatgccaa agctagggtg gcccttgcag ttcagcacca ccctagtccc  1800 ttccctccc tggctcccat gaccatactg agggaccaac tgggcccaag acagatgccc   1860
cagagctgtt tatggcctca gctgcctcac ttcctacaag agcagcctgt ggcatctttg  1920
ccttgggctg ctcctcatgg tgggttcagg ggactcagcc ctgaggtgaa agggagctat  1980
caggaacagc tatgggagcc ccagggtctt ccctacctca ggcaggaagg gcaggaagga  2040
gagcctgctg catggggtgg ggtagggctg actagaaggg ccagtcctgc ctggccaggc  2100
agatctgtgc cccatgcctg tccagcctgg gcagccaggc tgccaaggcc agagtggcct  2160
ggccaggagc tcttcaggcc tccctctctc ttctgctcca cccttggcct gtctcatccc  2220
caggggtccc agccacccccg ggctctctgc tgtacatatt tgagactagt ttttattcct  2280
tgtgaagatg atatactatt tttgttaagc gtgtctgtat ttatgtgtga ggagctgctg  2340
gcttgcagtg cgcgtgcacg tggagagctg gtgcccggag attggacggc ctgatgctcc  2400
ctcccctgcc ctggtccagg gaagctggcc gagggtcctg gctcctgagg ggcatctgcc  2460 cctccccaa cccccacccc acacttgttc cagctctttg aaatagtctg tgtgaaggtg  2520
aaagtgcagt tcagtaataa actgtgttta ctcagtgaaa aaaaaaaaa aaaaa        2575
```

Preferably, in situ hybridization is used to detect the presence of chromosomal copy number increase or gene amplification at the Bcl-2 locus, as well as the loci defined by probes A_67_P04742617 and A_83_P174456 (Available from Agilent (Santa Clara, Calif.); mouse CGH microarray 244A, catalog number G4415A). Probes can be made by one of skill in the art using the sequences of SEQ ID NO:1.

Probes for use in the in situ hybridization methods of the invention fall into two broad groups: chromosome enumeration probes, i.e., probes that hybridize to a chromosomal region, usually a repeat sequence region, and indicate the presence or absence of an entire chromosome; and locus specific probes, i.e., probes that hybridize to a specific locus on a chromosome and detect the presence or absence of a specific locus. Chromosome arm probes, i.e., probes that hybridize to a chromosomal region and indicate the presence or absence of an arm of a specific chromosome, can also be used. It is preferred to use a locus specific probe that can detect changes of the unique chromosomal DNA sequences at the interrogated locus such as Bcl-x$_L$. Methods for use of unique sequence probes for in situ hybridization are described in U.S. Pat. No. 5,447,841, incorporated herein by reference.

A chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. Centromere fluorescent in situ hybridization probes to each of chromosomes 14 and 18 are commercially available from Abbott Molecular (Des Plaines, Ill.).

Exceptionally useful in situ hybridization probes are directly labeled fluorescent probes, such as described in U.S. Pat. No. 5,491,224, incorporated herein by reference. U.S. Pat. No. 5,491,224 also describes simultaneous FISH assays using more than one fluorescently labeled probe.

Useful locus specific probes can be produced in any manner and generally contain sequences to hybridize to a chromosomal DNA target sequence of about 10,000 to about 1,000,000 bases long. Preferably the probe hybridizes to a target stretch of chromosomal DNA at the target locus of at least 100,000 bases long to about 500,000 bases long and also includes unlabeled blocking nucleic acid in the probe mix, as disclosed in U.S. Pat. No. 5,756,696, herein incorporated by reference, to avoid non-specific binding of the probe. It is also possible to use unlabeled, synthesized oligomeric nucleic acid or peptide nucleic acid as the blocking nucleic acid. For targeting the particular gene locus, it is preferred that the probes include nucleic acid sequences that span the gene and thus hybridize to both sides of the entire genomic coding locus of the gene. The probes can be produced starting with human DNA-containing clones such as Bacterial Artificial Chromosomes (BAC's) or the like. BAC libraries for the human genome are available from Invitrogen (Carlsbad, Calif.) and can be investigated for identification of useful clones. It is preferred to use the University of California Santa Cruz Genome Browser to identify DNA sequences in the target locus. These DNA sequences can then be used to synthesize PCR primers for use to screen BAC libraries to identify useful clones. The clones can then be labeled by conventional nick translation methods and tested as in situ hybridization probes.

Examples of fluorophores that can be used in the in situ hybridization methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxy-coumarin-3-carboxylic acid; 6-[fluorescein 5-(and-6)-carboxamido]hexanoic acid; N-(4, 4-difluoro-5,7-dimethyl-4-bora-3a,4a diaza-3-indacenepropionic acid; eosin-5-isothiocyanate; erythrosine-5-isothiocyanate; 5-(and-6)-carboxyrhodamine 6G; and Cascade™ blue aectylazide (Molecular Probes; an Invitrogen brand).

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems. Alternatively, techniques such as flow cytometry can be used to examine the hybridization pattern of the chromosomal probes.

Although the cell-by-cell gene amplification analysis resulting from in situ hybridization is preferred, the genomic biomarkers can also be detected by quantitative PCR. In this embodiment, chromosomal DNA is extracted from the tissue sample, and is then amplified by PCR using a pair of primers specific to at least one of Bcl-2, Bcl-$x_L$ or Bcl-w, or by multiplex PCR, using multiple pairs of primers. Any primer sequence for the biomarkers can be used. The copy number of the tissue is then determined by comparison to a reference amplification standard.

Microarray copy number analysis can also be used. In this embodiment, the chromosomal DNA after extraction is labeled for hybridization to a microarray comprising a substrate having multiple immobilized unlabeled nucleic acid probes arrayed at probe densities up to several million probes per square centimeter of substrate surface. Multiple microarray formats exist and any of these can be used, including microarrays based on BAC's and on oligonucleotides, such as those available from Agilent Technologies (Palo Alto; CA), and Affymetrix (Santa Clara; CA). When using an oligonucleotide microarray to detect amplifications, it is preferred to use a microarray that has probe sequences to more than three separate locations in the targeted region.

Detecting Expression: mRNA

The level of gene expression of Bcl-$x_L$ can be determined by assessing the amount of one or more mRNAs in the test sample. Methods of measuring mRNA in samples are known in the art. To measure mRNA levels, the cells in a test sample can be lysed, and the levels of mRNA in the lysates or in RNA purified or semi-purified from lysates can be measured by any variety of methods familiar to those in the art. Such methods include hybridization assays using detectably labeled DNA or RNA probes (i.e., Northern blotting) or quantitative or semi-quantitative RT-PCR methodologies using appropriate oligonucleotide primers. Alternatively, quantitative or semi-quantitative in situ hybridization assays can be carried out using, for example, tissue sections, or unlysed cell suspensions, and detectably labeled (e.g., fluorescent, or enzyme-labeled) DNA or RNA probes. Additional methods for quantifying mRNA include RNA protection assay (RPA), cDNA and oligonucleotide microarrays, representation difference analysis (RDA), differential display, EST sequence analysis, and serial analysis of gene expression (SAGE).

In suitable embodiments, PCR amplification is used to detect Bcl-$x_L$ gene in the test sample. Briefly, in PCR, two primer sequences are prepared that are complementary to regions on opposite complementary strands of the marker sequence, e.g., Bcl-$x_L$ gene. An excess of deoxynucleotide triphosphates are added to a reaction mixture along with a DNA polymerase, e.g., Taq polymerase. If the target sequence is present in a sample, the primers will bind to the sequence and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated, thereby generating amplification products. A reverse transcriptase PCR amplification procedure can be performed in order to quantify the amount of mRNA amplified.

Any suitable fragment of Bcl-$x_L$ gene can be amplified and detected. Designing efficient primers for PCR is within the ordinary skill in the art. Typically, amplified fragments for detection are approximately 50 to 300 nucleotides in length.

Amplification products can be detected in several ways. Amplification products can be visualized by electrophoresis of the sample in a gel and then staining with a DNA binding dye, e.g., ethidium bromide. Alternatively, the amplification products can be integrally labeled with a radio- or fluorescence nucleotide and then visualized using x-ray film or under the appropriate stimulating spectra.

Amplification can be also monitored using "real-time" methods. Real time PCR allows for the detection and quantitation of a nucleic acid target. Typically, this approach to quantitative PCR utilizes a fluorescent dye, which can be a double-strand specific dye, such as SYBR GREEN®. I. Alternatively, other fluorescent dyes (e.g., FAM or HEX) can be conjugated to an oligonucleotide probe or a primer. Various instruments capable of performing real time PCR are known in the art and include, for example, the ABI PRISM® 7900 (Applied Biosystems) and LIGHTCYCLER® systems (Roche). The fluorescent signal generated at each cycle of PCR is proportional to the amount of PCR product. A plot of fluorescence versus cycle number is used to describe the kinetics of amplification and a fluorescence threshold level is used to define a fractional cycle number related to initial template concentration. When amplification is performed and detected on an instrument capable of reading fluorescence during thermal cycling, the intended PCR product from nonspecific PCR products can be differentiated using melting analysis. By measuring the change in fluorescence while gradually increasing the temperature of the reaction subsequent to amplification and signal generation it can be possible to determine the Tm of the intended product(s) as well as that of the nonspecific product.

The methods can include amplifying multiple nucleic acids in sample, also known as "multiplex detection" or "multiplexing." "Multiplex PC" refers to PCR that involves adding more than one set of PCR primers to the reaction in order to detect and quantify multiple nucleic acids, including nucleic acids from one or more target gene markers. Furthermore, multiplexing with an internal control (e.g., 18S rRNA, GADPH, or O-actin) provides a control for the PCR without reaction.

Detecting Expression: Polypeptides

The methods and assays of the invention are also directed in parting to evaluation polypeptide expression, such as monitoring Bcl-$x_L$ polypeptide expression. The amount of the expression of the polypeptides can be assessed, either qualitatively or quantitatively. In other embodiments, the amount of expression of the polypeptides is compared between non-tumor or cancer cells and tumor or cancer cells. Any method known in the art can be used for this, but especially convenient are immunoassays, wherein antibodies that specifically bind to Bcl-$x_L$ polypeptide is used. Examples of commercially available anti-Bcl-$x_L$ antibodies is shown in Table 3.

TABLE 3

Commercially available anti-Bcl-$x_L$ antibodies

| Antigen | Source | Catalog no. | Type* |
|---|---|---|---|
| Bcl-$x_L$ | Trevigen (Gaithersburg, MD) | 2300-MC | mAb |
| | Calbiochem (San Diego, CA) | AM05 | mAb |
| | Sigma (St. Louis, MO) | B9429 | mAb |
| | AnaSpec (San Jose, CA) | 54177 | pAb |

*mAb, monoclonal antibody; pAb, polyclonal antibody.

There are two basic types of immunoassays, competitive and non-competitive (e.g., immunometric and sandwich, respectively). In both assays, antibody or antigen reagents are covalently or non-covalently attached to the solid phase. Linking agents for covalent attachment are known and can be part of the solid phase or derivatized to it prior to coating. Examples of solid phases used in immunoassays are porous and non-porous materials, latex particles, magnetic particles, microparticles, strips, beads, membranes, microtiter wells and plastic tubes. The choice of solid phase material and method of detectably labeling the antigen or antibody reagent are determined based upon desired assay format performance characteristics. For some immunoassays, no detectable label is required. For example, if the antigen is on a detectable particle such as a red blood cell, reactivity can be established based upon agglutination. Alternatively, an antigen-antibody reaction can result in a visible change (e.g., radial immunodiffusion). In most cases, one of the antibody or antigen reagents used in an immunoassay is attached to a signal generating compound (detectable label). This signal generating compound or label is in itself detectable or can be reacted with one or more additional compounds to generate a detectable product (see also U.S. Pat. No. 6,395,472 B1). Examples of such signal generating compounds include chromogens, radioisotopes (e.g., $^{125}I$, $^{131}I$, $^{32}P$, $^{3}H$, $^{35}S$, and $^{14}C$), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound, and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent can recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

Any of the exemplary formats herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

The assays and kits of the present invention can be adapted or optimized for point of care assay systems, including Abbott's Point of Care (i-STAT™) electrochemical immunoassay system Immunosensors and methods of manufacturing and operating them in single-use test devices are described, for example in U.S. Pat. No. 5,063,081 and published U.S. Patent Application Nos. 20030170881, 20040018577, 20050054078, and 20060160164 (incorporated by reference herein for their teachings regarding same).

Sample Processing and Assay Performance

The tissue sample to be assayed by the inventive methods can comprise any type, including a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample. For example, a patient peripheral blood sample can be initially processed to extract an epithelial cell population, and this extract can then be assayed. A microdissection of the tissue sample to obtain a cellular sample enriched with suspected tumor cells can also be used. The preferred tissue samples for use herein are peripheral blood, tumor tissue or suspected tumor tissue, including fine needle aspirates, fresh frozen tissue and paraffin embedded tissue, and bone marrow.

The tissue sample can be processed by any desirable method for performing in situ hybridization or other nucleic acid assays. For the preferred in situ hybridization assays, a paraffin embedded tumor tissue sample or bone marrow sample is fixed on a glass microscope slide and deparaffinized with a solvent, typically xylene. Useful protocols for tissue deparaffinization and in situ hybridization are available from Abbott Molecular Inc. (Des Plaines, Ill.). Any suitable instrumentation or automation can be used in the performance of the inventive assays. PCR based assays can be performed on the m2000 instrument system (Abbott Molecular, Des Plaines, Ill.). Automated imaging can be used for the preferred fluorescent in situ hybridization assays.

In one embodiment, the sample comprises a peripheral blood sample from a patient which is processed to produce an extract of circulating tumor or cancer cells having an amplification at the Bcl-$x_L$ locus. The circulating tumor cells can be separated by immunomagnetic separation technology such as that available from Immunicon (Huntingdon Valley, Pa.). The number of circulating tumor cells showing at least one copy number gain is then compared to the baseline level of circulating tumor cells having increased copy number determined preferably at the start of therapy. Increases in the number of such circulating tumor cells can indicate therapy failure.

Test samples can comprise any number of cells that is sufficient for a clinical diagnosis, and typically contain at least about 100 cells. In a typical FISH assay, the hybridization pattern is assessed in about 25-1,000 cells. Test samples are typically considered "test positive" when found to contain the gene amplification in a sufficient proportion of the sample. The number of cells identified with chromosomal copy number and used to classify a particular sample as positive, in general, varies with the number of cells in the sample. The number of cells used for a positive classification is also known as the cut-off value. Examples of cut-off values that can be used in the determinations include about 5, 25, 50, 100 and 250 cells, or 5%, 10%, 15%, 20%, 25%, 30%, 35%, 40%, 50% and 60% of cells in the sample population. As low as one cell can be sufficient to classify a sample as positive. In a typical paraffin embedded tissue sample, it is preferred to identify at least 30 cells as positive and more preferred to identify at least 20 cells as positive for having the chromosomal copy number gain. For example, detection in a typical paraffin embedded small cell lung cancer tissue of 30 cells having a Bcl-$x_L$ amplification would be sufficient to classify the tissue as positive and eligible for treatment.

Assay Kits

In another aspect, the invention comprises kits for the detection of the genomic biomarkers that comprise containers containing at least one probe specific for binding to Bcl-$x_L$. These kits may also include containers with other associated reagents for the assay. Preferred kits of the invention comprise containers containing, respectively, at least one FISH probe capable of binding specifically to Bcl-$x_L$. The inventive kits can comprise nucleic acid probe analogs, such as peptide nucleic acid probes. Finally, the kits can further comprise instructions for use.

REFERENCES

Ashman, J. N., J. Brigham, M. E. Cowen, et al. 2002. Chromosomal alterations in small cell lung cancer revealed by multicolour fluorescent in situ hybridization. *Int J. Cancer.* 102:230-6.

Ausubel, F. M., R. Brent, R. E. Kingston, et al. 1987. Current protocols in molecular biology. John Wiley & Sons, New York.

Buchardt, O., P. Nielsen, and R. Berg. 1992. PEPTIDE NUCLEIC ACIDS.

Chaudhary, K. S., P. D. Abel, and E. N. Lalani. 1999. Role of the Bcl-2 gene family in prostate cancer progression and its implications for therapeutic intervention. *Environ Health Perspect.* 107 Suppl 1:49-57.

Cobleigh, M. A., C. L. Vogel, D. Tripathy, et al. 1999. Multinational study of the efficacy and safety of humanized anti-HER2 monoclonal antibody in women who have HER2-overexpressing metastatic breast cancer that has progressed after chemotherapy for metastatic disease. *J Clin Oncol.* 17:2639-48.

Coe, B. P., E. H. Lee, B. Chi, et al. 2006. Gain of a region on 7p22.3, containing MAD1L1, is the most frequent event in small-cell lung cancer cell lines. *Genes Chromosomes Cancer.* 45:11-9.

Cory, S., D. C. Huang, and J. M. Adams. 2003. The Bcl-2 family: roles in cell survival and oncogenesis. *Oncogene.* 22:8590-607.

Fan, Y.-S. 2002. Molecular cytogenetics: protocols and applications. Humana Press, Totowa, N.J. xiv, 411 p. pp.

Fino, J. U.S. Pat. No. 5,464,746. 1995. HAPTENS, TRACERS, IMMUNOGENS AND ANTIBODIES FOR CARBAZOLE AND DIBENZOFURAN DERIVATIVES.

Galteland, E., E. A. Sivertsen, D. H. Svendsrud, et al. 2005. Translocation t(14;18) and gain of chromosome 18/BCL2: effects on BCL2 expression and apoptosis in B-cell non-Hodgkin's lymphomas. *Leukemia.* 19:2313-23.

Jeffers, J. R., E. Parganas, Y. Lee, et al. 2003. Puma is an essential mediator of p53-dependent and -independent apoptotic pathways. *Cancer Cell.* 4:321-8.

Kim, Y. H., L. Girard, C. P. Giacomini, et al. 2006. Combined microarray analysis of small cell lung cancer reveals altered apoptotic balance and distinct expression signatures of MYC family gene amplification. *Oncogene.* 25:130-8.

Lynch, T. J., D. W. Bell, R. Sordella, et al. 2004. Activating mutations in the epidermal growth factor receptor underlying responsiveness of non-small-cell lung cancer to gefitinib. *N Engl J Med.* 350:2129-39.

Martinez-Climent, J. A., A. A. Alizadeh, R. Segraves, et al. 2003. Transformation of follicular lymphoma to diffuse large cell lymphoma is associated with a heterogeneous set of DNA copy number and gene expression alterations. *Blood.* 101:3109-17.

Mattingly, P. U.S. Pat. No. 5,424,414. 1995. HAPTENS, TRACERS, IMMUNOGENS AND ANTIBODIES FOR 3-PHENYL-A-ADAMANTANEACETIC ACIDS.

Monni, I., H. Joensuu, K. Franssila, et al. 1996. DNA copy number changes in diffuse large B-cell lymphoma—comparative genomic hybridization study. *Blood.* 87:5269-78.

Mullis, K., F. Faloona, S. Scharf, et al. 1986. Specific enzymatic amplification of DNA in vitro: the polymerase chain reaction. *Cold Spring Harb Symp Quant Biol.* 51 Pt 1:263-73.

Nielsen, P. E., M. Egholm, R. H. Berg, et al. 1991. Sequence-selective recognition of DNA by strand displacement with a thymine-substituted polyamide. *Science.* 254:1497-500.

Nupponen, N. N., L. Kakkola, P. Koivisto, et al. 1998. Genetic alterations in hormone-refractory recurrent prostate carcinomas. *Am J Pathol.* 153:141-8.

Ohmori, T., E. R. Podack, K. Nishio, et al. 1993. Apoptosis of lung cancer cells caused by some anti-cancer agents (MMC, CPT-11, ADM) is inhibited by bcl-2. *Biochem Biophys Res Commun.* 192:30-6.

Olejniczak, E. T., C. Van Sant, M. G. Anderson, et al. 2007. Integrative genomic analysis of small-cell lung carcinoma reveals correlates of sensitivity to bcl-2 antagonists and uncovers novel chromosomal gains. *Mol Cancer Res.* 5:331-9.

Oltersdorf, T., S. W. Elmore, A. R. Shoemaker, et al. 2005. An inhibitor of Bcl-2 family proteins induces regression of solid tumours. *Nature.* 435:677-81.

Pauletti, G., S. Dandekar, H. Rong, et al. 2000. Assessment of methods for tissue-based detection of the HER-2/neu alteration in human breast cancer: a direct comparison of fluorescent in situ hybridization and immunohistochemistry. *J Clin Oncol.* 18:3651-64.

Ruth, J. U.S. Pat. No. 4,948,882. 1990. Ruth, J. 1990. SINGLE-STRANDED LABELED OLIGONUCLEOTIDES, REACTIVE MONOMERS AND METHODS OF SYNTHESIS.

Shibue, T., K. Takeda, E. Oda, et al. 2003. Integral role of Noxa in p53-mediated apoptotic response. *Genes Dev.* 17:2233-8.

van Delft, M. F., A. H. Wei, K. D. Mason, et al. 2006. The BH3 mimetic ABT-737 targets selective Bcl-2 proteins and efficiently induces apoptosis via Bak/Bax if Mcl-1 is neutralized. *Cancer Cell.* 10:389-99.

van der Krol, A. R., J. N. Mol, and A. R. Stuitje. 1988. Modulation of eukaryotic gene expression by complementary RNA or DNA sequences. *Biotechniques.* 6:958-76.

Villunger, A., E. M. Michalak, L. Coultas, et al. 2003. p53- and drug-induced apoptotic responses mediated by BH3-only proteins puma and noxa. *Science.* 302:1036-8.

Yasui, K., S. Mihara, C. Zhao, et al. 2004. Alteration in copy numbers of genes as a mechanism for acquired drug resistance. *Cancer Res.* 64:1403-10.

Zon, G. 1988. Oligonucleotide analogues as potential chemotherapeutic agents. *Pharm Res.* 5:539-49.

We claim:

1. A method for identifying a patient with small-cell lung carcinoma or a lymphoma as eligible to receive N-(4-(4-((2-(4-chlorophenyl)-5,5-dimethyl-1-cyclohex-1-en-1-yl)methyl) piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide therapy or an anti-sense agent designed to bind to one of Bcl-2, Bcl-w, and Bcl-$x_L$ comprising:

(a) providing a tissue sample from a patient;
(b) determining if expression of a Bcl-$x_L$ gene is amplified relative to a baseline control level determined before the administration of N-(4-(4-((2-(4-chlorophenyl)-5,5-dimethyl-1-cyclohex-1-en-1-yl)methyl)piperazin-1-yl) benzoyl)-4-(((1R)-3-(morpholin-4-yl)-1-((phenylsulfanyl)methyl)propyl)amino)-3-((trifluoromethyl) sulfonyl)benzenesulfonamide;
(c) identifying the patient as eligible to receive N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl) benzenesulfonamide or the anti-sense agent designed to bind to one of Bcl-2, Bcl-w, and Bcl-$x_L$ if the Bcl-$x_L$ gene is not amplified; and
(d) administering N-(4-(4-((2-(4-chlorophenyl)-5,5-dimethyl-1-cyclohex-1-en-1-yl)methyl)piperazin-1-yl) benzoyl)-4-(((1R)-3-(morpholin-4-yl)-1-((phenylsulfanyl)methyl)propyl)amino)-3-((trifluoromethyl) sulfonyl)benzenesulfonamide or the anti-sense agent designed to bind to one of Bcl-2, Bcl-w, and Bcl-$x_L$ to the patient identified as being eligible to receive N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl) amino)-3-((trifluoromethyl)sulfonyl) benzenesulfonamide or the anti-sense agent designed to bind to one of Bcl-2, Bcl-w, and Bcl-$x_L$.

2. The method of claim 1, wherein amplification of the Bcl-$x_L$ gene correlates with an increase in expression of Bcl-$x_L$ polypeptide.

3. The method of claim 1, wherein the tissue sample comprises a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample.

4. The method of claim 1, wherein the determining step comprises in situ hybridization.

5. The method of claim 4, wherein the in situ hybridization is performed with a nucleic acid probe that is detectably labeled.

6. The method of claim 4, wherein the in situ hybridization is performed with a nucleic acid probe or peptide nucleic acid probe that specifically hybridizes to at least part of the Bcl-$x_L$ gene.

7. The method of claim 1, wherein determining comprises a polymerase chain reaction.

8. The method of claim 7, wherein the polymerase chain reaction is performed with at least one primer that specifically hybridizes to at least part of a nucleic acid sequence of the Bcl-$x_L$ gene.

9. The method of claim 1, wherein the determining step comprises a nucleic acid microarray assay.

10. A method for identifying a patient with small-cell lung carcinoma or a lymphoma as eligible to receive N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide therapy or an anti-sense agent designed to bind to one of Bcl-2, Bcl-w, and Bcl-$x_L$ comprising:
(a) providing a test sample from a patient;
(b) determining in the test sample:
(i) if a Bcl-$x_L$ gene is amplified relative to a baseline control level determined before the administration of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide; and
(ii) an amount of Bcl-$x_L$ in the test sample;
(c) determining if the amount of Bcl-$x_L$ in the test sample is higher or lower than the amount of Bcl-$x_L$ in a control, wherein the control is a level determined before the administration of N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide; and
(d) identifying the patient as eligible to receive N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or the anti-sense agent designed to bind to one of Bcl-2, Bcl-w, and Bcl-$x_L$ therapy based on:
(i) amplification of the Bcl-$x_L$ gene; and
(ii) the amount of Bcl-$x_L$ is higher in the test sample than in the control; and
(e) administering N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or the anti-sense agent designed to bind to one of Bcl-2, Bcl-w, and Bcl-$x_L$ to the patient identified as being eligible to receive N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or the anti-sense agent designed to bind to one of Bcl-2, Bcl-w, and Bcl-$x_L$.

11. The method of claim 10, wherein the test sample comprises a peripheral blood sample, a tumor tissue or a suspected tumor tissue, a thin layer cytological sample, a fine needle aspirate sample, a bone marrow sample, a lymph node sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample, a paraffin embedded tissue sample or an extract or processed sample produced from any of a peripheral blood sample, a tumor tissue or a suspected tumor tissue, a thin layer cytological sample, a fine needle aspirate sample, a bone marrow sample, a urine sample, an ascites sample, a lavage sample, an esophageal brushing sample, a bladder or lung wash sample, a spinal fluid sample, a brain fluid sample, a ductal aspirate sample, a nipple discharge sample, a pleural effusion sample, a fresh frozen tissue sample or a paraffin embedded tissue sample.

12. The method of claim 10, wherein determining amplification of the Bcl-$x_L$ gene comprises in situ hybridization.

13. The method of claim 12, wherein the in situ hybridization is performed with a nucleic acid probe that is detectably labeled.

14. The method of claim 12, wherein the in situ hybridization is performed with a nucleic acid probe or peptide nucleic acid probe that specifically hybridizes to at least part of the Bcl-$x_L$ gene.

15. The method of claim 10, wherein determining amplification of the Bcl-$x_L$ gene comprises a polymerase chain reaction.

16. The method of claim 15, wherein the polymerase chain reaction is performed with at least one primer that specifically hybridizes to at least part of a nucleic acid sequence of the Bcl-$x_L$ gene.

17. The method of claim 10, wherein the determining step comprises a nucleic acid microarray assay.

18. The method of claim 10, wherein the determining step (b)(ii) is performed by immunoassay.

19. The method of claim 18, wherein the immunoassay is a sandwich immunoassay.

20. The method of claim 18, wherein the immunoassay is an ELISA.

21. The method of claim 18, wherein the determining step (b)(ii) is performed on an automated immunoassay instrument.

22. The method of claim 10, wherein the determining step (b)(ii) is performed by measuring Bcl-$x_L$ mRNA.

* * * * *

UNITED STATES PATENT AND TRADEMARK OFFICE
CERTIFICATE OF CORRECTION

PATENT NO. : 9,045,800 B2
APPLICATION NO. : 12/704165
DATED : June 2, 2015
INVENTOR(S) : Semizarov et al.

It is certified that error appears in the above-identified patent and that said Letters Patent is hereby corrected as shown below:

In the Claims:

Column 25, line 8, claim 7: "wherein determining" to read as --wherein the determining step--

Column 26, line 28, claim 12: "wherein determining" to read as --wherein the determining--

Column 26, line 38, claim 12: "wherein determining" to read as --wherein the determining--

Signed and Sealed this
Twenty-sixth Day of July, 2016

Michelle K. Lee
*Director of the United States Patent and Trademark Office*